United States Patent [19]

Steudle et al.

[11] Patent Number: 5,211,055
[45] Date of Patent: May 18, 1993

[54] APPARATUS FOR THE SELECTIVE DETERMINATION OF THE CONCENTRATION OF A SUBSTANCE DISSOLVED IN A SOLVENT

[75] Inventors: Ernst Steudle, Eckersdorf; Gerd Böling, Inden; Josef Zillikens, Jülich, all of Fed. Rep. of Germany

[73] Assignee: Kernforschungsanlage Lülich Gesellschaft mit beschränkter Haftung, Jülich, Fed. Rep. of Germany

[21] Appl. No.: 724,792

[22] Filed: Jul. 2, 1991

Related U.S. Application Data

[62] Division of Ser. No. 263,422, Oct. 27, 1988, Pat. No. 5,141,873.

[30] Foreign Application Priority Data

Oct. 27, 1987 [DE] Fed. Rep. of Germany ....... 3736230

[51] Int. Cl.[5] ............................................. G01N 13/04
[52] U.S. Cl. .................................................. 73/64.47
[58] Field of Search ....................................... 73/64.47

[56] References Cited

U.S. PATENT DOCUMENTS 4,666,672 5/1987 Miller et al. ........................... 422/68
4,706,495 11/1987 Steudle et al. ......................... 73/64.3
4,891,968 1/1990 Steudle et al. ......................... 73/64.3

FOREIGN PATENT DOCUMENTS 56-155831 12/1981 Japan .
1029951 5/1966 United Kingdom .

Primary Examiner—Tom Noland
Assistant Examiner—Joseph W. Roskos
Attorney, Agent, or Firm—Nils H. Ljungman and Associates

[57] ABSTRACT

This invention relates to an apparatus for the selective determination of the concentration of a substance dissolved in a solvent by means of an osmosis cell. The osmosis cell according to the invention contains a substance not contained in the solution to be tested, which is either practically insoluble or is impermeable for the membrane. This substance reacts chemically with the substance permeating into the osmosis cell, with a product resulting from it in the cell or with a product resulting from the substance in the solution to be tested and permeating into the cell. Reaction products are thereby formed which produce a pressure in the osmosis cell, which is different from the osmotic pressure of the chemically converted portion of the substance. A pressure increase thereby occurs in the cell, from which the concentration of the substance in the solution to be tested can be determined on the basis of standard values.

11 Claims, 10 Drawing Sheets

APPARATUS FOR THE SELECTIVE DETERMINATION OF THE CONCENTRATION OF A SUBSTANCE DISSOLVED IN A SOLVENT

This is a division of application Ser. No. 07/263,422, filed on Oct. 27, 1988 now U.S. Pat. No. 5,141,873.

BACKGROUND OF THE INVENTION

1. Field of the Invention

The field of the invention relates to a process for the selective determination of the concentration of a substance (A) dissolved in a solvent by means of an osmotic cell having a rigid wall with a pressure measurement apparatus for the measurement of the hydrostatic pressure in the osmotic cell, and with a membrane which is permeable for the substance, by means of which the osmometer solution in the osmotic cell is brought into contact with the solution, the concentration of the substance in which is to be determined. First, using a reference solution brought into contact with the osmometer solution by means of the membrane, a working pressure $P_0$ is established whereupon, after the replacement of the reference solution with the solution to be tested, the concentration of the permeable substance (A) in the solution to be tested is determined from the pressure curve which is established in the osmotic cell. The field of the invention also relates to apparatus for the performance of the process.

2. Description of the Prior Art

U.S. Pat. No. 4,706,495 entitled "Method and Apparatus for the Determination of Substances Dissolved in a Solvent", which corresponds to German Laid Open Patent Appln. No. 35 25 668, describes processes using an osmotic cell of the type described above, according to which the concentration of substances in a solution to be tested is determined from the pressure curve established in the osmotic cell. These patent publications, supra, are incorporated herein by reference as if the entire contents thereof were set forth herein.

The osmotic cell used has a rigid wall and also a rigid membrane, so that during the process, the change in the volume of the osmotic cell is very small.

The processes of the prior art of course make it possible to determine the concentration of a substance in a solution, if there are two or more substances in the solution. For this purpose, however, it is necessary to evaluate a large portion of the pressure curve established after the exchange of the solutions, up to the final pressure, or to use two osmotic cells with different membranes.

OBJECT OF THE INVENTION

The object of the invention is a process for the determination of the concentration of a substance dissolved in a solvent, which makes possible a selective determination of the concentration of this material.

SUMMARY OF THE INVENTION

This object may be achieved with a process of the type described above, by means of a method of operating an osmotic cell for the selective determination of the concentration of a substance (A) dissolved in a solvent said an osmotic cell having a rigid partition with a pressure measurement apparatus to measure the hydrostatic pressure in the osmotic cell, and with a membrane which is permeable for the substance, across which the osmometer solution in the osmotic cell is brought into contact with the solution, the concentration of the substance in which is to be determined, in which first, using a reference solution brought into contact with the osmometer solution across the membrane, a working pressure $P_0$ is established, and then after replacing the reference solution with the solution to be tested, the concentration of the permeable substance (A) in the solution to be tested is determine from the pressure curve recorded in the osmotic cell, characterized by the fact that the osmometer solution contains a substance (B) not contained in the reference solution and the solution to be tested, which substance B is either practically insoluble or is impermeable with regard to the membrane, and which reacts chemically with the substance (A) permeated in the osmotic cell, a product (H) arising from it in the cell, or from a product (G) arising in the solution to be tested from the substance (A) and permeated into the cell, whereby reaction products (C, D, E) are formed, which produce an osmotic pressure in the cell, which is different from the osmotic pressure of the chemically reacted portion of the substance (B), so that a pressure change takes place in the cell, from which the concentration of the substance (A) in the solution can be determined on the basis of standard values.

The membrane of the cell should preferably therefore be as permeable as possible for the substance to be measured (or for G) (reflection coefficient $\sigma < < 1$; high rate constant $k_s$), while it can also preferably be as impermeable as possible for the reaction products ($\sigma \approx 1$; low $k_s$) or alternatively as permeable as possible.

In the first case, a pressure increase will be measured; in the second case, a pressure decrease will be measured. In each case it must preferably be assured, however, that the determining factor for the rate is the passage through the membrane and not the preceding or subsequent chemical reaction.

Since the pressure change measured in the osmotic cell is caused essentially by water displacements between the solution and the cell, the rate constant $K_w$ for the water exchange must also preferably be sufficiently high.

In addition, the time constants for the mixing process in the osmotic cell and in the solution must preferably be low in relation to the time constants for the water exchange of the osmotic cell. That is the case if the $K_w$ value of the osmotic cell:

$$K_w = \frac{A_o}{V_o} \cdot L_p \cdot (\epsilon + \pi_o^i)$$

where
$A_o$ is the effective surface of the membrane,
$V_o$ is the volume of the osmotic cell,
$L_p$ is the hydraulic conductivity of the membrane
$\epsilon$ is the volume modulus of elasticity of the osmotic cell, and
$\pi_o^i$ is the osmotic pressure in the cell is preferably sufficiently great. This can be achieved by selecting a suitable osmotic cell, since for the factors:

$$\frac{A_o}{V_o},$$

$L_p$ and $\epsilon$ it is a question of design-specific values of an osmotic cell or its membrane. On the other hand, the initially linear path of the pressure/time curve established as the result of a concentration change must be sufficiently long compared to the duration of the mixing phase which occurs during the exchange of the two solutions in the measurement system.

The process described by one embodiment of the invention is essentially characterized by the fact that the effective osmotic concentration in the osmotic cell is changed as a result of the chemical reaction of the substance A to be measured (or a product of it) with a practically impermeable substance B in the osmometer, where B can be present as a dissolved substance or as a solid substance with a defined solubility. The change of the osmotic concentration in the cell causes water flows through the membrane, which lead to pressure changes. These in turn are a yardstick for the concentration of the substance A in the solution to be tested. The process of this one embodiment is appropriately regulated so that after the replacement of the reference solution with the solution to be tested, the initial slope $(dP/dt)t=0$ of the pressure/time curve reflecting the pressure change in the osmotic cell is determined. The pressure changes in the osmotic cell can be caused by the sum of the osmotic concentrations $C_i$ of the reaction products $C_i$, with reference to their reflection coefficients $\sigma_i$, i.e. $\Sigma \sigma_i C_i$, differ sufficiently from that of the osmotic substance B in the initial state. Thus both a pressure increase and a pressure decrease can be indicated. The pressure changes, for example, can be caused by the fact that the reaction products are permeable and quickly leave the cell through the membrane, so that the osmotic concentration decreases continuously as a result of the consumption of substance B in the cell. In one embodiment they can also be caused by the fact that a practically insoluble solid is dissolved in the osmometer and impermeable products are formed, which cause a pressure increase.

To be able to determine the concentration of substance A in the solution to be tested with the greatest possible accuracy, the substance B should preferably react as selectively as possible with substance A. However, it can also be a complex reaction in which, instead of only one substance B, two (or more) substances interact, and produce reaction products in the reaction with substance A. The important thing is that a pressure change is produced in the osmotic cell, which is a yardstick for the concentration of substance A in the solution to be tested. It is thereby important that preferably the passage through the membrane is what governs the rate of the entire process, and not the preceding or subsequent chemical reactions.

For a precise determination of substance A, it is also necessary to make certain, by an appropriate membrane selection, that other substances contained in the solution to be tested (or which cannot be tested in the time available), do not get into the osmotic cell. It may also be necessary to previously remove interfering substances, e.g. by way of a chemical treatment (precipitation) from the solution to be tested. At the same time, for a precise determination of substance A, the concentration of this substance in the solution to be tested should only be so high that the proportion of substance A or of the products G, H resulting from it which get into the osmotic cell after the replacement of the reference solution with the solution to be tested are chemically reacted, and the pressure curve established in the cell results exclusively from the difference in the osmotic pressures of the consumed portion of substance B and the reaction products C, D and E which are formed. The substance B must also be selected so that the permeation of the substance A, i.e. its passage through the membrane, is the factor which determines the rate of the pressure change.

While avoiding disturbing influences, the process according to an embodiment of the invention can also be used for the determination of trace substances A which are present in the solution in a concentration of less than $10^{-3}$M.

For a determination of standard curves, solutions with known concentrations of substance A are used, whereby complications caused by other substances can be avoided. The specified determination of substance A can thereby be verified in terms of its accuracy, if the solutions used as standard solutions also contain the other substances found in the solution to be tested in the specified concentrations.

A solution which contains all the substances in the specified concentration except for substance A is appropriately used as a reference solution to establish the working pressure $P_0$. The osmotic effects of the secondary substances in the solution to be tested are thereby eliminated.

If a substance B is used which is present in the osmotic cell as a solid substance with only low solubility, the working pressure $P_0$ is then zero. If a different working pressure is desired, then it can be achieved by the addition of an impermeable substance added to the osmometer solution which does not participate in the reaction.

Various cases can be distinguished for the performance of the process described by the invention.

The simplest case is one in which the substance A gets into the osmotic cell and reacts there with substance B. If we call the substances found in the solution to be tested L, and the substances in the osmotic cell Z, then this simple case can be described as follows:

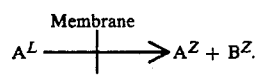

This leads to:

A practical example is the determination of permeable hydrogen sulfide ($H_2S$) by means of mercury (II) cyanide ($Hg(CN)_2$) as the impermeable substance B:

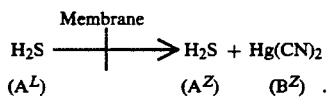

$H_2S$ easily permeates into the osmotic cell. $Hg(CN)_2$ is present in the osmotic cell practically undissociated.

The HgS formed in the reaction:

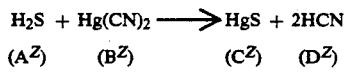

precipitates, while the hydrogen cyanide (HCN) formed, quickly leaves the osmotic cell with a sufficiently acid pH. A measurable pressure decrease thereby occurs in the osmotic cell.

Mercury (II) cyanide does not react with many reagents $Hg^{2+}$ ions. The reaction is therefore largely selective for hydrogen sulfide.

Another practical example for the simple case is the determination of ammonia ($NH_3$) with the use of relatively insoluble silver chloride (AgCl) as substance B:

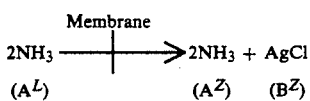

according to the equation:

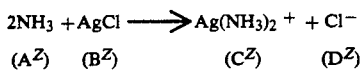

for each $NH_3$ molecule absorbed, an osmotically effective ion is formed in the osmotic cell.

It can be shown that the sensitivity of the proof of the complex-forming agent (here: $NH_3$) is a function of the solubility product of the insoluble salt (B). Salts which are relatively insoluble (e.g. AgCl in the indicated example) are less suitable than more easily soluble salts (e.g. $Ag_2CrO_4$). Salts with an excessively low solubility product are generally unsuitable. For example, silver iodide (AgI) would probably be unsuitable for the determination of $NH_3$, since it does not dissolve in the presence of $NH_3$. Silver iodide, on the other hand, is generally suitable for the determination of cyanide ($CN^-$, since the $Ag(CN)_2^-$ complexes are significantly more stable. The example shows how a selectivity ($CN^-$ in relation to $NH_3$) can be achieved by a suitable selection of the solid substances (salts) in complex formation.

The latter example illustrates the use of the process described by the invention for the measurement of ammonia in drinking water in which there are only negligible amounts of other substances. The selective determination of the ammonia can therefore be performed very precisely.

In another case, a product is formed in the osmotic cell from substance A which leads to the selective determination of A:

The reaction in the cell, as indicated, can be accelerated by a catalyst ($K^Z$).
That leads to:

The catalyst $K^Z$ can be an enzyme, for example.

A practical example is the determination of urea by means of an osmotic cell which is permeable for this substance, which contains urease as catalyst and a buffer. The ammonia formed by the hydrolysis of urea in the cell is converted by means of the buffer into a relatively impermeable salt, which increases the osmolality of the cell and leads to a pressure increase.

In another case, a product formed in the solution to be tested from substance A permeates into the osmotic cell and reacts there with substance B:

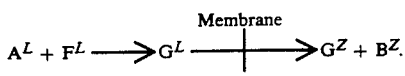

This leads to:
$G^Z + B^Z \rightarrow$ reaction products.

A practical example is the determination of urea described in more detail in Embodiment 4, in which ammonia is formed by means of an enzyme ($F^L$), permeates into the osmotic cell and leads to pressure changes there.

To perform the process, an apparatus is used which has a vessel and a measurement head which, for example, is preferably apparatus for the selective determination of the concentration of a substance (A) dissolved in a solvent, for the performance of the processes described supra and infra, with a vessel and a measurement head, which comprises an osmotic cell in which there is an inlet and outlet valve for the admission and discharge of the osmometer solution, and a pressure measurement apparatus, which has a rigid metal or plastic wall, and the rigid membrane of which is also permeable for the substance, whereby the ratio of the volume of the osmotic cell to the effective surface of the membrane is a maximum 0.2 mm, whereby the measurement head can be immersed in the vessel and the vessel can be charged alternatively with a reference solution to set the working pressure $P_0$, with the solution to be tested, and if necessary also with standard solutions, characterized by the fact that the inlet and outlet valves for the admission and discharge of the osmometer solution are designed and configured so that the volume of the portions of the line extending from the cell to the valve closing is as small as possible and that the wall of the osmotic cell is at least partly covered with a solid substance (B) and/or the osmotic cell contains the substance (B), which chemically reacts with the substance (A) when the latter enters the cell or with a product (G, H) of this reaction, and thereby forms reaction products (C, D, E), which when the process is conducted in the cell produce an osmotic pressure which is different from the osmotic pressure of the chemically converted portion of substance (B).

Substance B can be dissolved in the osmometer solution, and is then filled with it into the osmotic cell. However, it can also be a solid substance, which is added to the osmotic cell as such. It can either be placed in the cell as a paste, or it can be part of the cell wall, so that it is an integral component of the cell. The use of solid substances is advantageous to the extent that it improves the volume/surface ratio (and thus the $K_w$ and $k_s$ values), so that V/A becomes significantly less than 0.2 mm.

Since the substance B found in the osmometer solution is consumed, from time to time the cell must be filled with fresh osmometer solution. One type of apparatus which is particularly suited for performing the process according to the invention therefore exhibits the characteristics described supra. The valve system is designed so that the volume of the cell is practically not substantially increased. Of course, it must be designed so that there is a sufficiently rapid throughput.

Depending on the volumetric proportion of the solid substance B placed in the cell, the unfilled cell itself can have a volume greater than would correspond to the ratio of volume to effective surface indicated supra.

Any unstirred layers which may occur in the cell are taken into consideration during the calibration with solutions of a specified concentration.

To carry out the process according to the invention, there is yet another embodiment of an apparatus with reservoirs and a measurement head which are included in apparatus for the determination of the concentration of a substance (A) dissolved in a solvent, for the performance of the processes described supra, with reservoirs and a measurement head, which comprises an osmotic cell with an inlet and outlet valve for the admission and discharge of the osmometer solution and with pressure measurement apparatus and a vessel, whereby the osmotic cell has a rigid metal or plastic wall as well as a membrane, also rigid, which is permeable for the substance, whereby the ratio of the volume of the osmotic cell to the effective surface of the membrane is a maximum 0.2 mm and whereby the vessel is in communication via the membrane with the osmotic cell, and is provided with a feed and discharge line for the reference solution to establish the working pressure $P_0$, for the solution to be tested and also, if necessary, for a standard solution, and the feed and discharge line of the vessel and the inside of the vessel are designed so that the solutions fed into them can be filled into the vessel of the measurement head as rapidly as possible, whereby storage vessels for the solution used to establish the working pressure $P_0$ are in communication with the feed line for the vessel of the measurement head, and also a reservoir or a pipeline containing the solution to be tested and in communication with the feed line for the vessel of the measurement head, characterized by the fact that the inlet and outlet valves for the admission and discharge of the osmometer solution are designed and configured so that the volume of the portions of the line extending from the cell to the valve closing is as small as possible and that the partition of the osmotic cell is at least partly covered by the substance (B) and/or the osmotic cell contains the substance (B) and/or the osmotic cell contains the substance (B), which chemically reacts with the substance 9A) when the latter enters the cell or with a product (G, H) of this reaction, and thereby forms reaction products (C, D, E), which when the process is conducted in the cell produce an osmotic pressure, which is different from the osmotic pressure of the chemically converted portion of substance (B). This apparatus, too, exhibits the above-mentioned characteristics relating to the valve system and the solid substance B in the cell.

The measurement head according to the first-named apparatus above preferably consists essentially of the osmotic cell and is designated "measurement head a". The measurement head of the second apparatus preferably consists essentially of osmotic cell and the vessel connected to it is designated "measurement head b".

Another aspect of the invention relates to an apparatus for the selective determination of the concentration of a substance (A) dissolved in a solvent, for the performance of the process having the following steps:

introducing a reference solution into the cell and bringing the reference solution into contact through the membrane with the osmometer solution on the side of the membrane opposite the reference solution, establishing a working pressure ($P_0$);

replacing the reference solution with the solution to be tested;

introducing into the cell at least one substance (B) not contained in the reference solution; the at least one substance (B) being at least one of:

practically insoluble, impermeable with regard to the membrane;

the at least one substance (B) reacting chemically with a chemical related to the substance (A) and producing at least one of the following products:

at least one product arising from the substance (B) in the cell, at least one product arising in the solution to be tested from the substance (A) and permeating the cell;

forming at least one reaction product which produces an osmotic pressure in the cell, which is different from the osmotic pressure of the chemically reacted portion of the substance (B), thereby producing a pressure change in the cell, from which the concentration of the substance (A) in the solution is determined.

the apparatus comprising:

a vessel and a measurement head, which comprise an osmotic cell in which there is an inlet and outlet valve for the admission and discharge of the osmometer solution, and a pressure measurement apparatus, which has a rigid wall made of at least one of the following materials:

metal, plastic;

the rigid membrane being permeable to at least one substance;

the measurement head being immersed in the vessel;

the vessel has arrangement for being charged alternatively with at least two of the following:

a reference solution to set the working pressure $P_0$, the solution to be tested, a standard solution;

the inlet and outlet valves for the admission and discharge of the osmometer solution providing a volume, of the portions of the line extending from the cell to the valve closing, which is minimized;

an arrangement for admitting at least one substance (B) comprising at least one of:

(a) an arrangement for at least partly covering the wall of the osmotic cell with a solid substance comprising substance (B), (b) an arrangement for containing the substance (B) in the osmotic cell, the substance for chemically reacting with at least one substance (A) at least during one of the following:

with substance (A) as it enters the cell, with a product of a reaction between substance (A) and substance (B) forming reaction products, which produce an osmotic pressure which is different from the osmotic pressure of the chemically converted portion of substance (B).

Embodiments of the measurement head (a, b) and embodiments of the apparatus according to the invention are illustrated schematically in the drawing, and are explained in greater detail below.

BRIEF DESCRIPTION OF THE DRAWINGS

The drawing also illustrates standard diagrams for embodiments of the process according to the invention.

DESCRIPTION OF THE PREFERRED EMBODIMENTS

Figure 1:
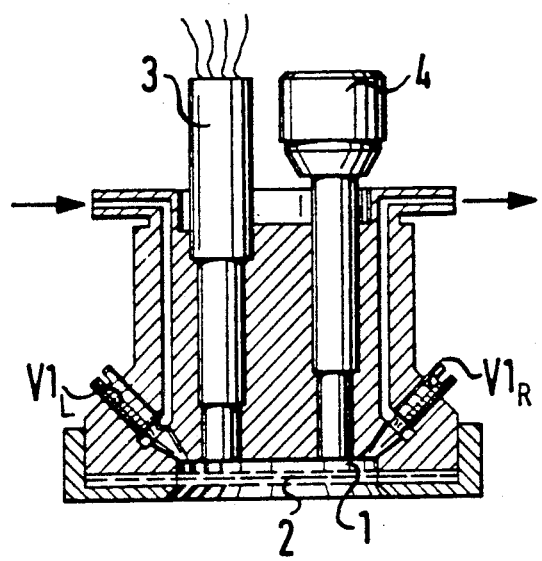
FIG. 1 shows a measurement head a, consisting of an osmotic cell with pressure measurement apparatus, and a micrometer screw with a control rod.

The measurement head a illustrated in FIG. 1 comprises an osmotic cell 1 with a membrane 2 and a pressure measurement apparatus 3 with a pressure transducer arrangement which generates an electrical signal. There is also an apparatus 4 for the controlled volume change of the osmotic cell 1, including a micrometer screw with a control rod, by means of which a measurable change in the volume of the osmotic cell can be brought about. This deliberate volume change, which results in a change in the pressure in the osmotic cell, can be used to measure the rigidity of the osmotic cell by means of the pressure measurenent transformer, or to determine the modulus of elasticity of the cell.

For a rapid replacement of the osmometer solution, there are valves V1 and V1R (an inlet and an outlet valve) which are directly adjacent to the osmotic cell 1, and which preferably increase its effective volume practically not at all.

Figure 2:
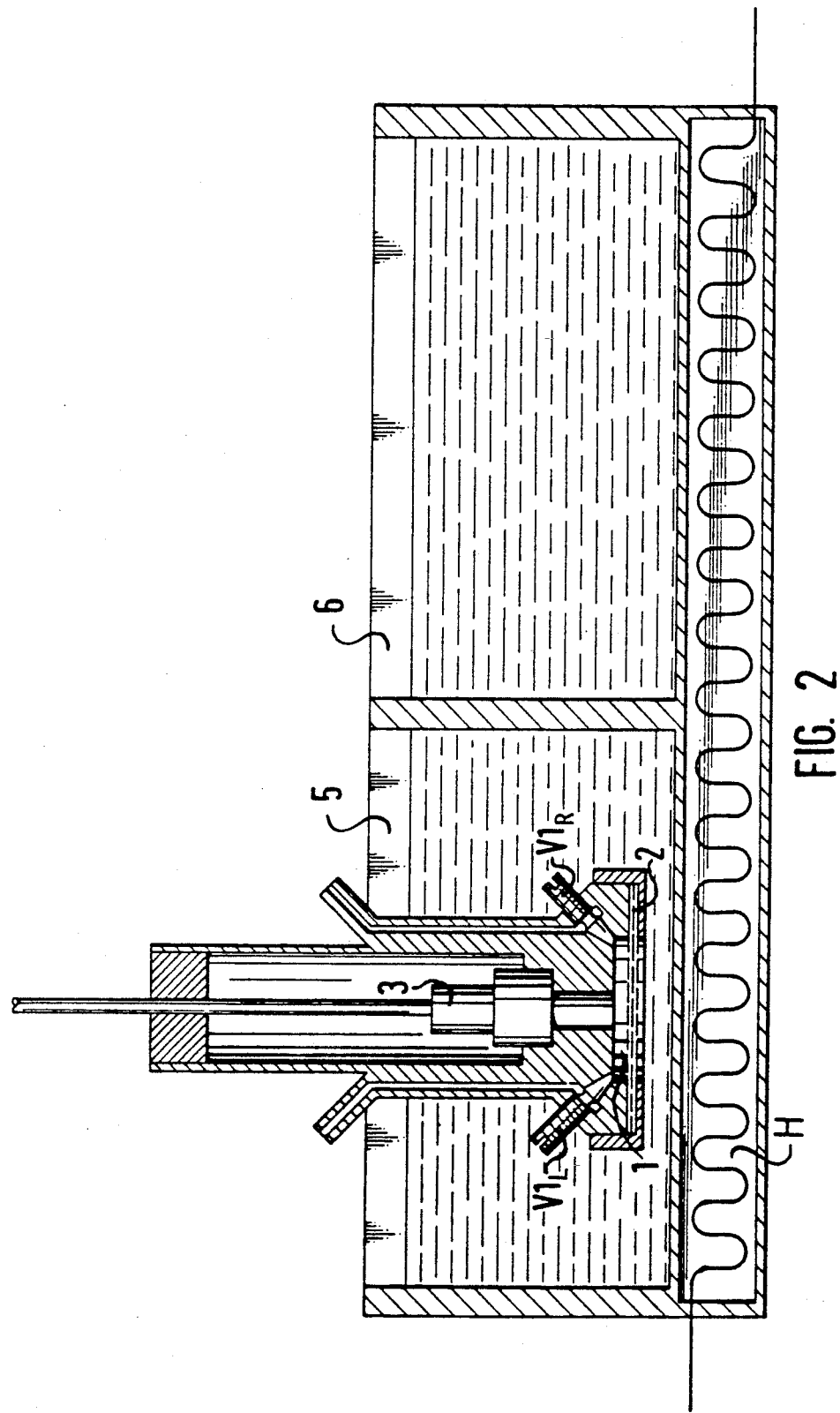
FIG. 2 shows an apparatus with a measurement head a, consisting of an osmotic cell with a pressure measurement apparatus.

FIG. 2 shows an apparatus with a measurement head a of the type illustrated in FIG. 1, including the osmotic cell 1 and the pressure measurement apparatus 3 in use. In this embodiment, there is no apparatus for controlled volume change.

There are optional vessels 5 and 6, for the reference solution and for the solution to be tested respectively. The solutions of the two vessels are preferably kept at a constant temperature by means of heater H controlled by a thermostat (not shown) well known in the art.

For the determination of the content of dissolved substance in the solution in the vessel 6, the measurement head is first immersed in the reference solution in the vessel 5 to determine the working pressure $P_0$. After the establishment and measurement of the working pressure $P_0$, the measuremend head is immersed in the solution to be tested in vessel 6 to carry out the process.

For calibration purposes, instead of the solution to be tested, a standard solution is used in the vessel 6.

Figure 3:
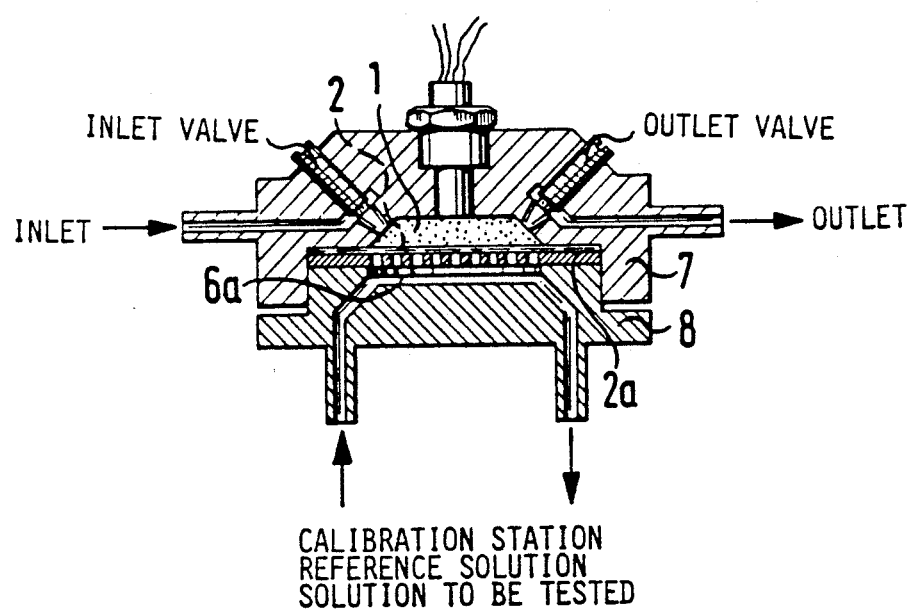
FIG. 3 shows a measurement head b, consisting of an osmotic cell and a vessel adjacent to the cell.

FIG. 3 shows a measurment head b with the osmotic cell 1, the membrane 2 with a support grid 2a and the pressure measurement apparatus 3, in which is integrated a vessel 6a to hold the solutions, and the housing of which, consisting of elements 7 and 8, is made of steel.

Figure 4:
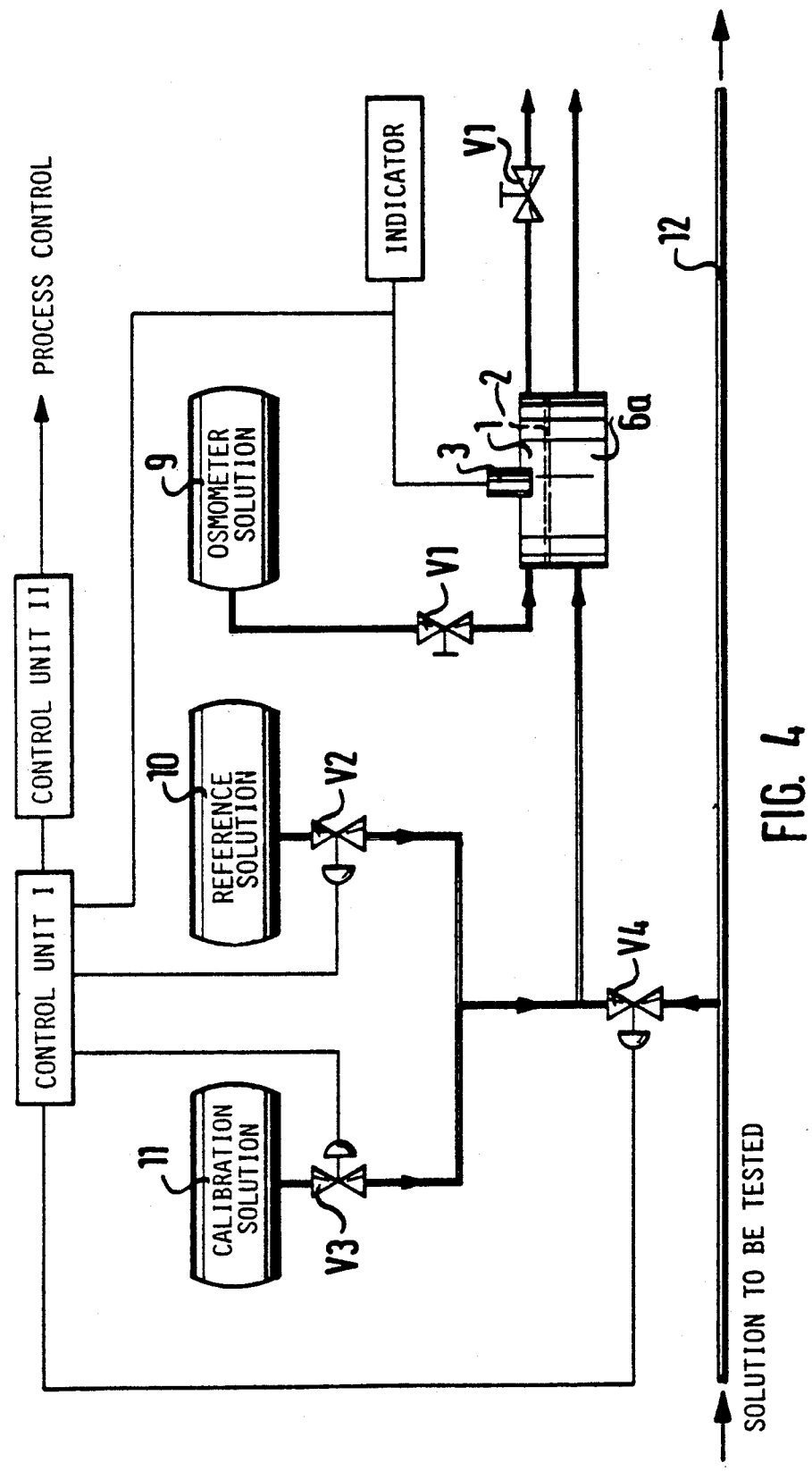
FIG. 4 shows an apparatus with measurement head b, as shown in FIG. 3, with automatic control of the measurement process, as well as a process control.

FIG. 4 illustrates an apparatus with a measurement head b of the type illustrated in FIG. 3.

When the valves V1 are open, osmometer solution is first introduced in the osmotic cell from the vessel 9. To establish the working pressure, a suitable reference solution from vessel 10 is then fed through the open valve V2 (valves V1, V3 and V4 are closed) from vessel 6a, whereby this solution is brought into contact with the osmometer solution in the osmotic cell across the membrane 2. Then, after establishment and determination of the working pressure $P_0$, with an open valve V4 (valves V1, V2 and V3 are closed), the solution to be tested is conducted from line 12 into the vessel 6a, whereupon there is a pressure change in the osmotic cell which is a yardstick for the concentration of the substance A in the solution. For calibration, a quantity of the standard calibration solution is fed from the vessel 11 through the valve V3, with valves V1, V2 and V4 closed to the vessel 6a.

Valves V1, V3 and V4 are designed as remote-control check valves, which are electrically connected to the control unit I. By means of this control unit I, at specified time intervals, to establish a working pressure $P_0$, reference solution from vessel 10 is fed into the vessel 6a via the valve V2 and then the solution to be tested is fed to the vessel 6a by the valve V4. Moreover, naturally, at greater intervals of time, the control unit I can also trip the feed of calibration solutions via valve V3 into the vessel 6a.

As shown in FIG. 4, moreover, the electrical output signals of the pressure measurement apparatus 3 can be indicated on a display or indicator 13 and received by the control unit I. The process is controlled by means of a control unit II, which is electrically connected to the control unit I, as a function of the measurements received.

Figure 5A:
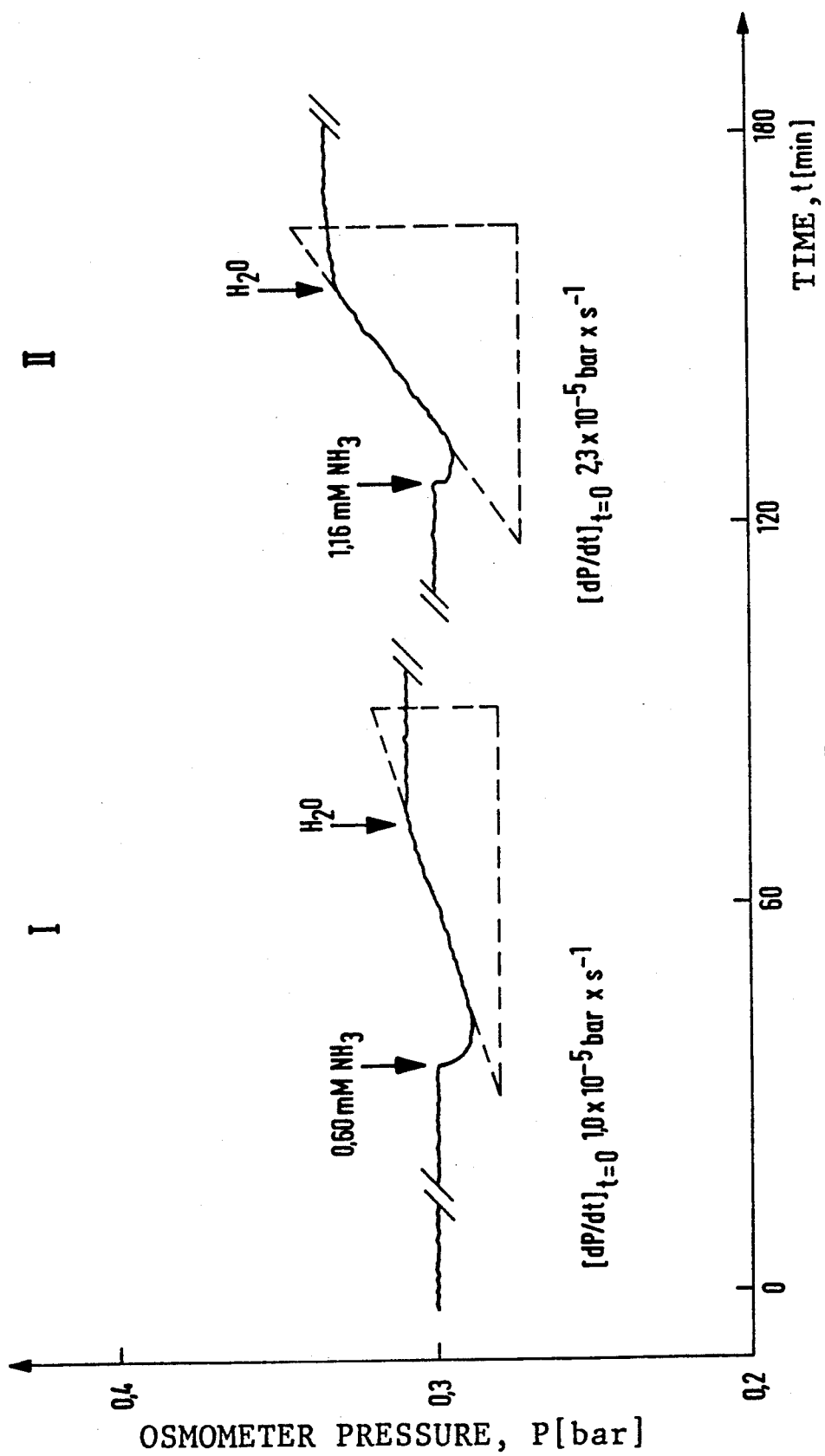
FIGS. 5a and 5b show the pressure curve in the osmotic cell during the measurement process.
Figure 5B:
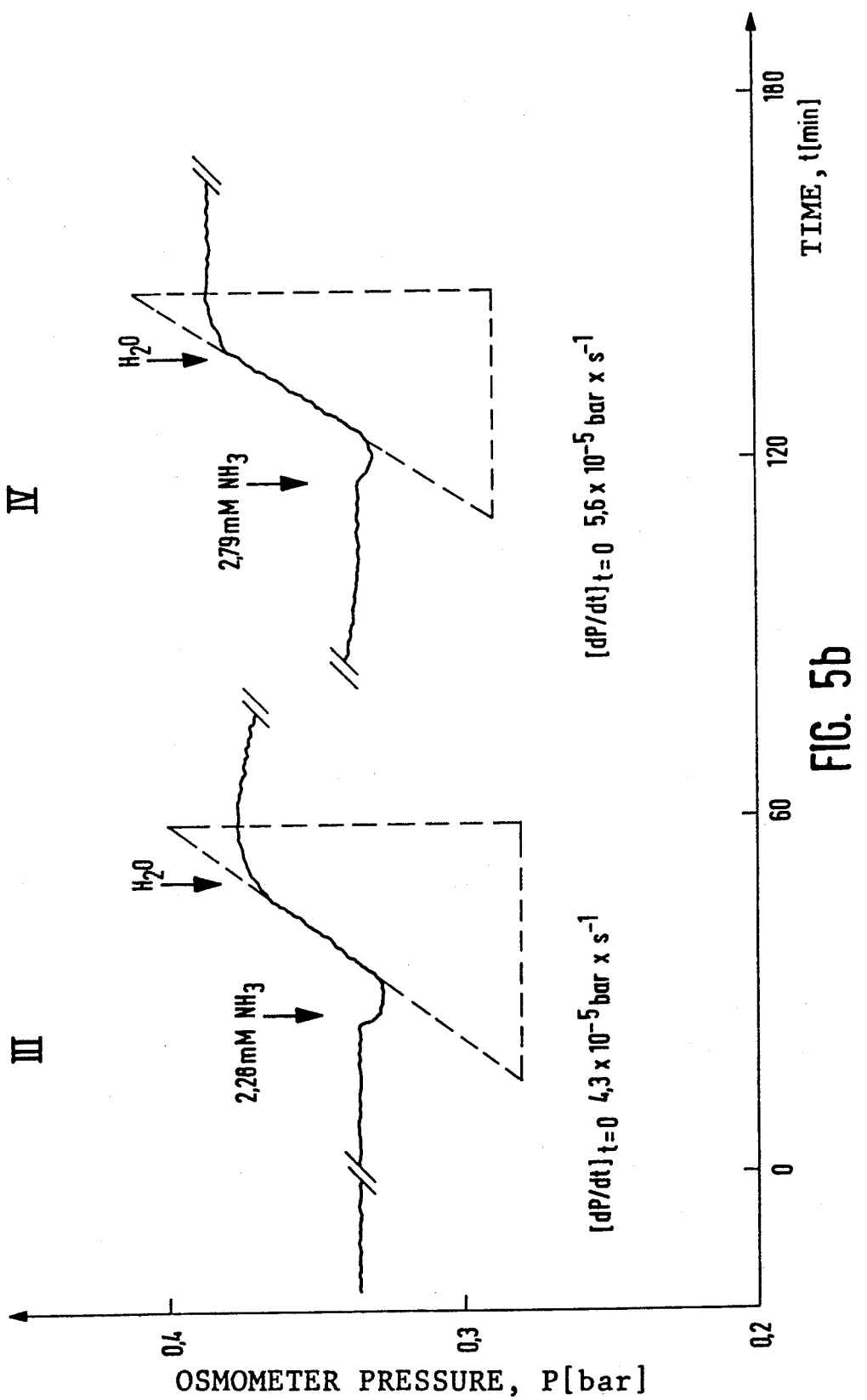

FIGS. 5a and 5b illustrate the pressure curve in the osmotic cell during the determination of ammonia with silver chromate as the solid, whereby the initial slope was determined for four different concentrations. The reference solution was distilled water. The low ammonia concentration causes an initial, small depression of the pressure, whereupon there is a very rapid onset of a constant pressure increase $((dP/dt)t=0)$. The four curves also indicate the slope triangles, by means of which the slopes were determined. Pressure/time curves of the type indicated were recorded during the calibration (See FIG. 6).

Embodiments

Using a measurement head of the type illustrated in FIG. 3, the solutions indicated below were tested. The measurement head was made of a stainless steel housing (layer thickness approximately 0.3 mm). In these embodiments the ratio of the volume of the osmotic cell to the effective surface of the membrane was 0.1 mm. It was filled with a paste containing $(Ag_2CrO_4)$ and water. The membrane was an asymmetrical polyamide membrane (reverse osmotic membrane) with a nominal separation limit of 50 Dalton. The solutions were kept at 25° C. for the measurement.

Figure 6:
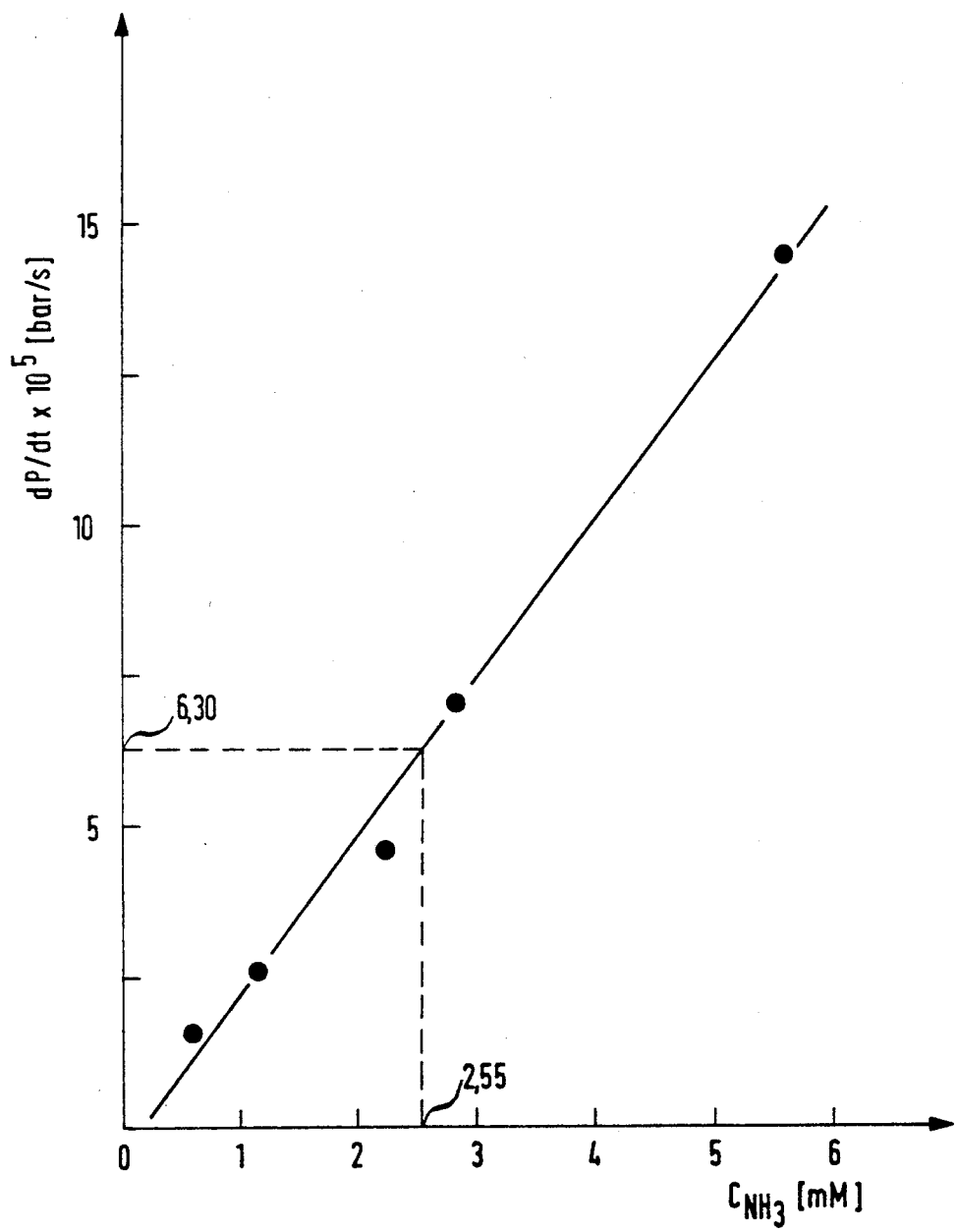
FIGS. 6 to 9 are standard diagrams corresponding to the embodiments 1 to 4 of FIGS. 1 to 4 respectively.

Embodiment 1:

To establish the standard curve indicated in FIG. 6, aqueous $NH_3$ solutions of various concentrations were used as standard solutions.

The $NH_3$ permeated into the osmotic cell caused the partial dissolution of the solid $(Ag_2CrO_4)$ according to the equation

$$Ag_2CrO_4 + 4NH_3 = 2Ag(NH_3)_2^+ + CrO_4^{2-}$$

The ions which were thereby formed are impermeable, which leads to a corresponding increase of the osmotic concentration and of the pressure in the osmotic cell, which is measured as a function of the time (measurement units: dP/dt in bar/s). As shown in FIG. 6, dP/dt for suitably low concentrations of $NH_3$ ($C_{NH_3}$)

is proportional to the concentration of $NH_3$ in the standard solution.

The solution to be tested, or test solution, was used, which contained 2.50 mM $NH_3$. The measured dP/dt of $6.3 \times 10^{-5}$ bar/s gave 2.55 mM $NH_3$ according to the standard curve. The reference solution was distilled water.

Figure 7:
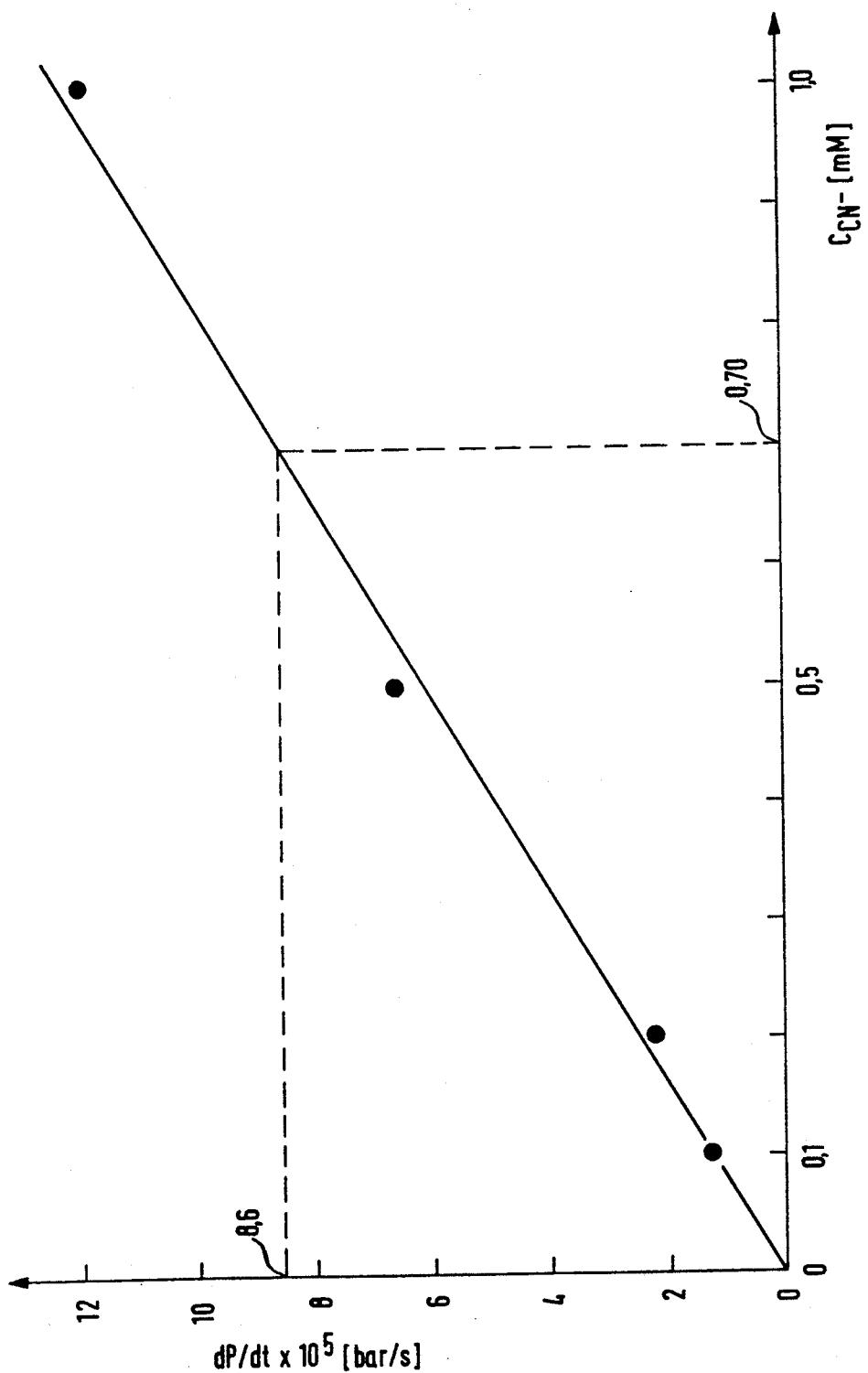

Embodiment 2:

To establish the standard curve indicated in FIG. 7, solutions of various concentrations were used as the standard solution (pH=8).

The KCN which permeates into the osmotic cell causes the dissolution of the $Ag_2CrO_4$ according to the equation

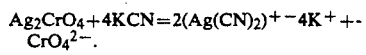

$$Ag_2CrO_4 + 4KCN = 2(Ag(CN)_2)^{+-}4K^+ +\text{-}CrO_4^{2-}.$$

with the formation of very solid silver cyanide complexes. The ions which are formed are practically impermeable.

A test solution was used which contained 0.73 mM $CN^-$. From this measured value for dP/dt of $8.6 \times 10^{-5}$ bar/s, the value of 0.70 mM $CN^-$ was determined on the basis of the standard curve. The reference solution was distilled water.

Embodiment 3:

The concentration of the relatively impermeable substance NaCl was determined, which causes a precipitation of the solid substance in the osmotic cell. To establish the standard curve indicated in FIG. 8, aqueous standard solutions with various concentrations were used.

The membrane used was also permeable (if not very) for univalent chloride ions. This characteristic could be used for a chloride determination. According to the equation $$Ag_2CrO_4 + 2\,NaCl = 2\,AgCl + 2\,Na^+ + CrO_4^{2-}$$

solid $Ag_2CrO_4$, which is significantly more soluble than silver chloride, was transformed into AgCl, whereby on each 2 $Cl^-$ ions, a bivalent $CrO_4^{2-}$ ion is formed.

This causes an increase in concentration and pressure in the osmometer, which increases with increasing concentration in the medium. For low concentrations of $C_{Cl^-}$ we find a nearly linear dependence of dP/dt on $C_{Cl^-}$.

Figure 8:
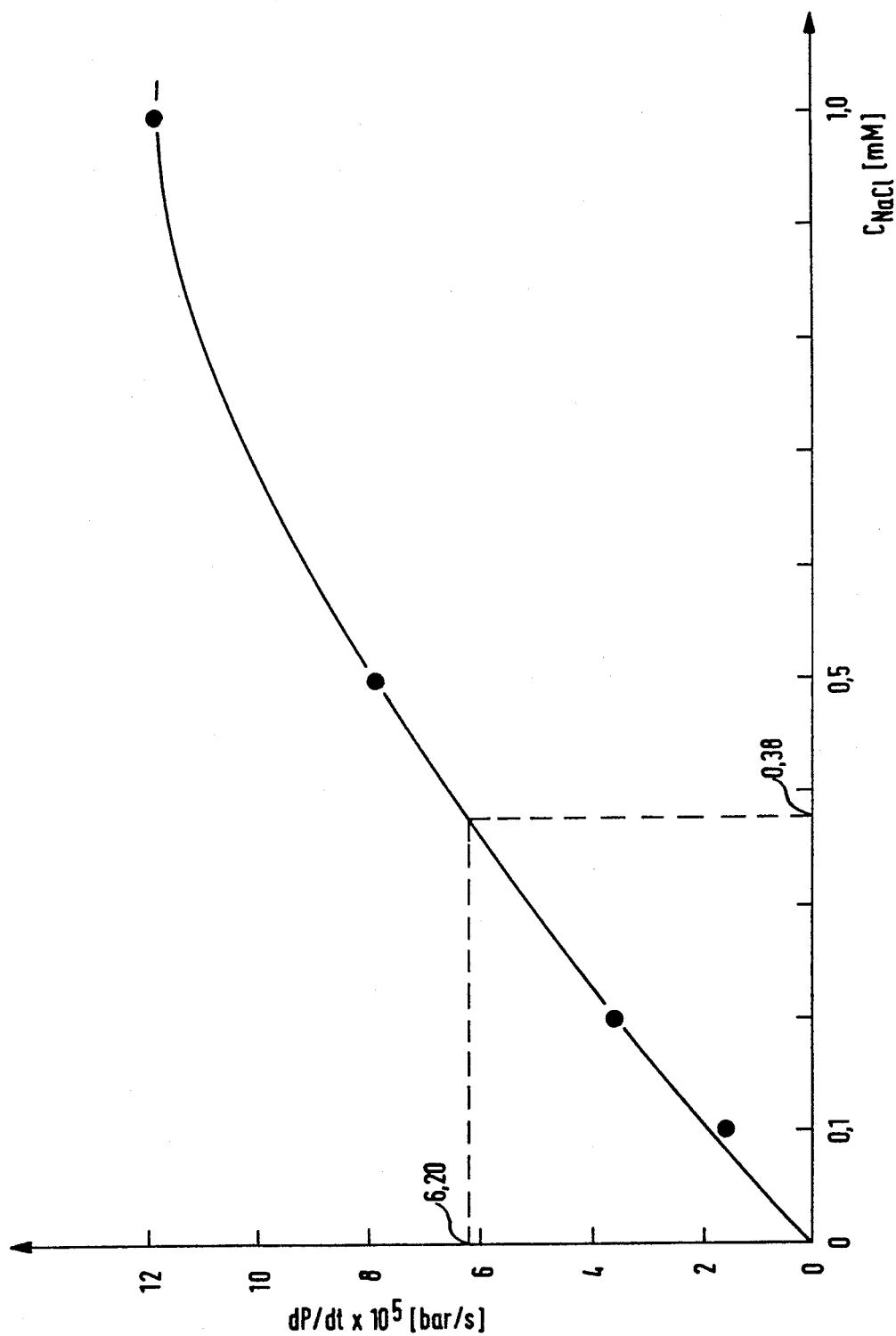

A solution of 0.40 mM NaCl was used as the test solution, which gave 0.38 mM $Cl^-$ according to the standard curve indicated in FIG. 8.

Embodiment 4:

The concentration of urea following a prior enzymatic hydrolysis with urease was determined, and the concentration of the ammonia formed was measured.

In the standard solutions (urea in aqueous solution), urea was hydrolyzed at 25° C. for 10 to 15 minutes in the of urease (20 units/10 ml). The pH of the solution was pH=8.7-9.3:

$$(NH_2)_2C = O + H_2O \xrightarrow{\text{urease}} CO_2 + 2NH_3.$$

Figure 9:
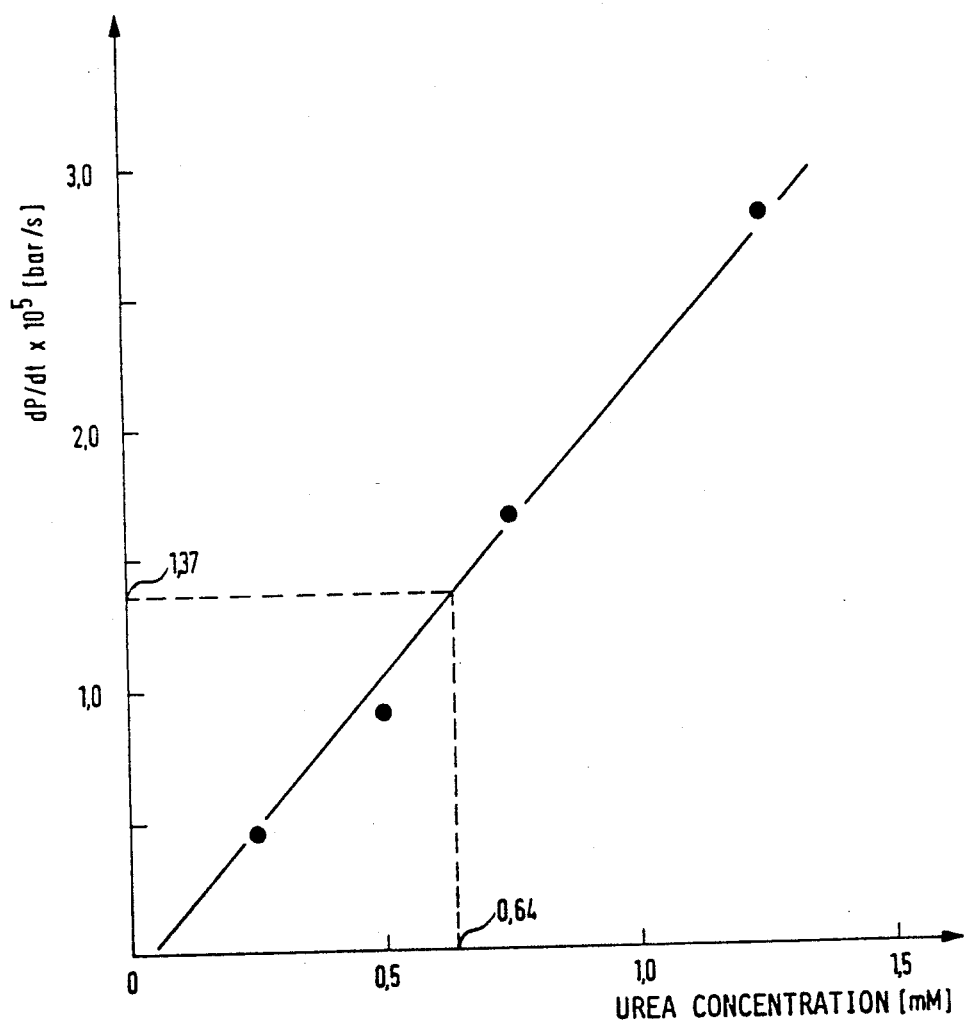

As in Embodiment 1, the ammonia formed, which permeates into the osmotic cell, was determined. FIG. 9 shows the standard curve for the determination of urea.

The test solution was an aqueous solution with 0.65 mM urea. It gave a dP/dt of $1.37 \times 10^{-5}$ bar/s, and a urea concentration of 0.64 mM.

In summing up, one aspect of the invention resides broadly in a process for the selective determination of the concentration of a substance (A) dissolved in a solvent by means of an osmosis cell having a rigid partition with a pressure measurement apparatus to measure the hydrostatic pressure in the osmosis cell, and with a membrane which is permeable for the substance, across which the osmometer solution in the osmosis cell is brought into contact with the solution, the concentration of the substance in which is to be determined, in which first, using a reference solution brought into contact with the osmometer solution across the membrane, a working pressure $P_0$ is established, and then after replacing the reference solution with the solution to be tested, the concentration of the permeable substance (A) in the solution to be tested is determined from the pressure curve recorded in the osmosis cell, characterized by the fact that the osmometer solution contains a substance (B) not contained in the reference solution and the solution to be tested, which substance (B) is either practically insoluble or is impermeable with regard to the membrane, and which reacts chemically with the substance (A) permeated in the osmosis cell, a product (H) arising from it in the cell, or from a product (G) arising in the solution to be tested from the substance (A) and permeated into the cell, whereby reaction products (C, D, E) are formed, which produce an osmotic pressure in the cell, which is different from the osmotic pressure of the chemically reacted portion of the substance (B), so that a pressure change takes place in the cell, from which the concentration of the substance (A) in the solution can be determined on the basis of standard values.

Another aspect of the invention resides broadly in a process, characterized by the fact that after the replacement of the reference solution with the solution to be tested, the initial slope $(dP/dt)t=0$ of the pressure/time/curve which reflects the pressure change in the osmosis cell is determined.

Yet another aspect of the invention resides broadly in a process characterized by the fact that the concentration of substance (A) in the solution to be tested is only so high that the portion of the substance (A) which gets into the osmosis cell after the replacement of the reference solution with the solution to be tested, or the resulting products (G, H) is rapidly converted chemically and the pressure curve recorded in the cell results solely from the difference of the osmotic pressures of the consumed portion of substance (B) and of the resulting reaction products (C, D, E).

A further aspect of the invention resides broadly in an apparatus for the selective determination of the concentration of a substance (A) dissolved in a solvent, for the performance of the process described above, with a vessel and a measurement head, which comprises an osmosis cell in which there is an inlet and outlet valve for the admission and discharge of the osmometer solution, and a pressure measurement apparatus, which has a rigid metal or plastic wall, and the rigid membrane of which is also permeable for the substance, whereby the ratio of the volume of the osmosis cell to the effective surface of the membrane is a maximum 0.2 mm, whereby the measurement head can be immersed in the vessel and the vessel can be charged alternatively with a reference solution to set the working pressure $P_0$, with the solution to be tested, and if necessary also with standard solutions, characterized by the fact that the inlet and outlet valves for the admission and discharge of the osmometer solution are designed and configured so that the volume of the portions of the line extending from the cell to the valve closing is as small as possible and that the wall of the osmosis cell is at least partly covered with a solid substance (B) and/or the osmosis cell contains the substance (B), which chemically reacts with the substance (A) when the latter enters the cell or with a product (G, H) of this reaction, and thereby forms reaction products (C, D, E), which when the process is conducted in the cell produce an osmotic pressure which is different from the osmotic pressure of the chemically converted portion of substance (B).

A yet further aspect of the invention resides broadly in an apparatus for the determination of the concentration of a substance (A) dissolved in a solvent, for the performance of the process described above, with reservoirs and a measurement head, which comprises an osmosis cell with an inlet and outlet valve for the admission and discharge of the osmometer solution and with pressure measurement apparatus and a vessel, whereby the osmosis cell has a rigid metal or plastic wall as well as a membrane, also rigid, which is permeable for the substance, whereby the ratio of the volume of the osmosis cell to the effective surface of the membrane is a maximum 0.2 mm and whereby the vessel is in communication via the membrane with the osmosis cell, and is provided with a feed and discharge line for the reference solution to establish the working pressure $P_0$, for the solution to be tested and also, if necessary, for a standard solution, and the feed and discharge line of the vessel and the inside of the vessel are designed so that the solutions fed into them can be filled into the vessel of the measurement head as rapidly as possible, whereby storage vessels for the solution used to establish the working pressure $P_0$ are in communication with the feed line for the vessel of the measurement head, and also a reservoir or a pipeline containing the solution to be tested and in communication with the feed line for the vessel of the measurement head, characterized by the fact that the inlet and outlet valves for the admission and discharge of the osmometer solution are designed and configured so that the volume of the portions of the line extending from the cell to the valve closing is as small as possible and that the partition of the osmosis cell is at least partly covered by the substance (B) and/or the osmosis cell contains the substance (B) and/or the osmosis cell contains the substance (B), which chemically reacts with the substance (A) when the latter enters the cell or with a product (G, H) of this reaction, and thereby forms reaction products (C, D, E), which when the process is conducted in the cell produce an osmotic pressure, which is different from the osmotic pressure of the chemically converted portion of substance (B).

What is claimed is:

1. Apparatus for the selective determination of a substance in a liquid, said apparatus comprising:
   an osmotic cell with an osmotic membrane;
   said cell comprising first and second chambers;
   said osmotic membrane being disposed between and dividing said cell into said first and second chambers;
   said osmotic membrane being rigid and permeable to at least a first substance;
   said second chamber having a pressure measurement head disposed therein measuring an osmotic pressure of a liquid in said second chamber;
   means for introducing a reference solution into said first chamber;
   means for removing the reference solution from said first chamber;
   means for introducing a calibration solution into said first chamber;
   means for removing a calibration solution from said first chamber;
   means for introducing a solution to be tested into said first chamber;
   means for removing the solution to be tested from said first chamber;
   means for introducing an osmometer solution into said second chamber;
   means for removing the osmometer solution from said second chamber;
   a second substance being disposed in said second chamber;
   said second substance for reacting with at least said first substance permeating through said membrane from said first chamber to said second chamber to produce at least a third substance; and
   said reacting of said second substance to produce said at least a third substance resulting in a greater change in osmotic pressure in said second chamber than a change in osmotic pressure by said first substance itself permeating into said second chamber.

2. The apparatus according to claim 1, wherein:
   said osmotic membrane has an effective surface area;
   said second chamber has a volume; and
   a ratio of the volume of the second chamber to the effective surface area of the membrane is a maximum of 0.2 mm.

3. The apparatus according to claim 2, wherein said first substance permeating through said membrane comprises one of:
   the substance to be selectively determined; and
   a product of a reaction of the substance to be selectively determined with a fourth substance.

4. The apparatus according to claim 3, wherein said second substance further reacts with a product of a reaction between the first substance permeating through the membrane and a fifth substance.

5. The apparatus according to claim 4, wherein said third substance produced by reacting said first substance with said second substance produces a greater increase in the osmotic pressure than said first substance itself.

6. The apparatus according to claim 5, wherein:
   said second chamber has at least one chamber wall; and
   said second substance comprises a solid disposed on at least a portion of the chamber wall of said second chamber.

7. The apparatus according to claim 6, wherein the pressure change measured in said second chamber results substantially only from a consumption of said second substance and a production of said third substance as the second substance reacts with said first substance to produce said third substance.

8. The apparatus according to claim 7, wherein:
   said means for introducing a reference solution into said first chamber, said means for introducing a calibration solution into said first chamber, and said means for introducing a solution to be tested into said first chamber comprise a single first valve;

said means for removing the reference solution from said first chamber, said means for removing a calibration solution from said first chamber, and said means for removing the solution to be tested from said first chamber comprise a single second valve; and said apparatus further comprises:
  means for recording a pressure curve representing the measured change in pressure in said second chamber to thereby determine the concentration of the substance to be selectively determined in the solution to be tested;
  means for obtaining at least one pressure versus time curve, after the replacement of the reference solution with the solution to be tested;
  means for determining the initial slope (dP/dt) at $t=0$ of the pressure versus time curve, which initial slope reflects the pressure change in the osmotic cell for determining the concentration of the substance to be selectively determined in the solution.

9. The apparatus according to claim 5, wherein said second substance is in solution with the osmometer solution before the osmometer solution is introduced into said second chamber.

10. The apparatus according to claim 9, wherein:
  the pressure change measured in said second chamber results substantially only from a consumption of said second substance and a production of said third substance as said second substance reacts with said first substance to produce said third substance; and the apparatus further comprises:
  means for recording a pressure curve representing the measured change in pressure in said second chamber to thereby determine the concentration of the substance to be selectively determined in the solution to be tested;
  means for obtaining at least one pressure versus time curve, after the replacement of the reference solution with the solution to be tested;
  means for determining the initial slope (dP/dt) at $t=0$ of the pressure versus time curve, which initial slope reflects the pressure change in the osmotic cell for determining the concentration of the substance to be selectively determined in the solution.

11. The apparatus according to claim 4, wherein said third substance produced by reacting said first substance with said second substance produces a greater decrease in the osmotic pressure than said first substance itself.

* * * * *

UNITED STATES PATENT AND TRADEMARK OFFICE
CERTIFICATE OF CORRECTION

PATENT NO. : 5,211,055
DATED : May 18, 1993
INVENTOR(S) : Ernst STEUDLE, Gerd BÜLING and Josef ZILLIKENS It is certified that error appears in the above-indentified patent and that said Letters Patent is hereby corrected as shown below:

On title page, item [73] Assignee; section, after 'Kernforschungsanlage', delete "Lülich" and insert --Jülich--.

In column 2, line 8, after 'is', delete "determine" and insert --determined--.

In column 4, line 67, after 'reagents', insert --for--.

In column 7, line 42, after 'substance', delete "9A)" and insert --(A)--.

In column 11, line 16, in the equation, after '$2(Ag(CN)_2)$', delete "+-" and insert -- $^-$+ --.

In column 12, line 41, before 'which', delete "time/curve" and insert --time curve--.

Signed and Sealed this

Twenty-fourth Day of May, 1994

BRUCE LEHMAN

Attest:

Attesting Officer

Commissioner of Patents and Trademarks